(12) United States Patent
McPherson et al.

(10) Patent No.: US 9,993,421 B2
(45) Date of Patent: Jun. 12, 2018

(54) METHOD FOR TREATING DELETERIOUS EFFECTS ARISING FROM TATTOOS

(71) Applicant: Go Tattless International, LLC, Queen Creek, AZ (US)

(72) Inventors: David A. McPherson, Queen Creek, AZ (US); James B. Severson, Jr., Florence, AZ (US); Samir Haggar, Scottsdale, AZ (US)

(73) Assignee: DYNAMO, LLC, Queen Creek, AZ (US)

( * ) Notice: Subject to any disclaimer, the term of this patent is extended or adjusted under 35 U.S.C. 154(b) by 0 days. days.

(21) Appl. No.: 15/356,043

(22) Filed: Nov. 18, 2016

(65) Prior Publication Data
US 2017/0143618 A1    May 25, 2017

Related U.S. Application Data

(60) Provisional application No. 62/258,330, filed on Nov. 20, 2015.

(51) Int. Cl.
| | |
|---|---|
| *A61K 8/97* | (2017.01) |
| *A61K 9/00* | (2006.01) |
| *A61K 36/886* | (2006.01) |
| *A61K 31/717* | (2006.01) |
| *A61K 8/73* | (2006.01) |
| *A61K 8/19* | (2006.01) |
| *A61Q 1/14* | (2006.01) |
| *A61M 37/00* | (2006.01) |
| *A61K 33/00* | (2006.01) |

(52) U.S. Cl.
CPC ............ *A61K 8/97* (2013.01); *A61K 8/19* (2013.01); *A61K 8/731* (2013.01); *A61K 9/0019* (2013.01); *A61K 31/717* (2013.01); *A61K 33/00* (2013.01); *A61K 36/886* (2013.01); *A61Q 1/145* (2013.01); *A61M 37/0084* (2013.01)

(58) Field of Classification Search
CPC .... A61K 2300/00; A61K 36/28; A61K 36/30; A61K 36/484; A61K 36/605; A61K 36/752; A61K 36/886; A61K 8/42; A61K 8/731; A61K 8/965; A61K 8/97; A61K 9/00; A61Q 1/145
See application file for complete search history.

(56) References Cited

U.S. PATENT DOCUMENTS

| | | |
|---|---|---|
| 6,932,966 B1 | 8/2005 | Kolos |
| 7,314,470 B2 | 1/2008 | Malodobry |
| 9,005,158 B2 | 4/2015 | Danenberg et al. |
| 2006/0142708 A1 | 6/2006 | Hazut et al. |
| 2009/0196840 A1* | 8/2009 | Lorenzo ............... A61K 31/167 424/59 |
| 2010/0247684 A1 | 9/2010 | Arnold-Ronish |
| 2010/0247687 A1* | 9/2010 | Arnold-Ronish ........ A61K 8/42 424/744 |
| 2012/0225914 A1* | 9/2012 | Sheena ................ A61K 31/135 514/357 |
| 2014/0094837 A1 | 4/2014 | Danenberg |
| 2014/0099296 A1 | 4/2014 | Covell |
| 2014/0106002 A1* | 4/2014 | Jensen ................ A61K 36/185 424/618 |

OTHER PUBLICATIONS

Islam et al (Clinical Reviews in Allergy and Immunology, Apr. 2016, vol. 50, pp. 273-286).*
Michael Pollitt, Now It's the Tata Tattoo, published online in the World section of Mail and Guardian on Aug. 3, 2007 <http://mg.co.za/article/2007-08-03-now-its-the-tata-tattoo> Retrieved on Nov. 16, 2016. pp. 1-2.
HomeRemediesForYou.com, Tattoo Natural Cures, published Nov. 28, 2007 <http://www.home-remedies-for-you.com/askquestion/11859/are-there-any-natural-cures-to-remove-tattoo.html> Retrieved on Nov. 16, 2016. pp. 1-2.
FDA.gov website, Consumer Health Information, published Oct. 2009 <http://www.fda.gov/downloads/ForConsumers/ConsumerUpdates/UCM143401.pdf>.
One in Five U.S. Adults Now Has a Tattoo, by Harris Interactive, published Feb. 23, 2012 <http://www.theharrispoll.com/health-and-life/One_in_Five_U_S_Adults_Now_Has_a_Tattoo.html> Retrieved on Nov. 17, 2016. pp. 1-9.
Eva Engel, Tattoo Pigments in Skin: Determination and Quantitative Extraction of Red Tattoo Pigments, Dissertation, Aug. 3, 2007 at the Institute for Organic Chemistry at the University of Regensburg, Germany.
Kimia Eghbali, Zahra Mousavi and Parisa Ziarati, Determination of Heavy Metals in Tattoo Ink, Apr. 19, 2014, p. No. 941-946, vol. 11, Issue 2, Biosciences Biotechnology Research Asia peer reviewed open access research journal, India. http://www.biotech-asia.org/absdoic.php?snoid=1363.

* cited by examiner

*Primary Examiner* — Mark V Stevens
(74) *Attorney, Agent, or Firm* — Barbara Luther; The Luther Law Firm, PLC

(57) ABSTRACT

A method of treating a medical condition resulting from a tattoo has the steps of cleaning at least one surface of the tattoo; preparing a plurality of needles to administer a formulation of a solution containing aloe, less than about 30% salt, carboxymethylcellulose and distilled water; covering the surface of the tattoo surrounding area with injections of the solution until the selected area has a different appearance; spreading the solution on the surface of the tattoo to provide a coating, and permitting the solution to dry. Preferably the salt is Himalayan salt.

6 Claims, 20 Drawing Sheets
(20 of 20 Drawing Sheet(s) Filed in Color)

METHOD FOR TREATING DELETERIOUS EFFECTS ARISING FROM TATTOOS

TECHNICAL FIELD

This invention relates generally to the removal of tattoos and, more specifically, to new formulas for removing tattoos from skin and a subsequent application method of using same.

BACKGROUND OF THE INVENTION

A tattoo is a permanent body modification made by inserting pigment or ink into the layers of skin to change the skin's normal pigmentation for decorative purposes or other reasons. The tattooing process involves the injection of pigment into the skin's dermis, the layer of connective tissue underlying the outer epidermis. After initial injection, pigment disperses throughout a homogeneous damaged layer down through the epidermis and upper dermis, in both of which the presence of foreign material activates the immune system's phagocytes to engulf the pigment particles. As healing proceeds, the damaged epidermis flakes away (eliminating surface pigment) and is replaced, while granulation forms deeper in the skin, which is later converted to connective tissue by collagen growth. This mends the upper dermis, where pigment remains trapped within fibroblasts, ultimately concentrating in a layer just below the dermis/epidermis boundary. Its presence there is stable, but in the long term (decades) the pigment tends to migrate deeper into the dermis, accounting for the degraded detail of old tattoos.

Many different dyes, inks and pigments and combinations typically are used in tattoos. They range from inorganic materials like titanium dioxide and iron oxides to carbon black, azo dyes, and acridine, quinoline, phthalocyanine and naphthol derivates, dyes made from ash, and other mixtures. Amateurs use any available vegetable or mineral for tattoos. The current trend for professional tattoo pigmentation utilizes a variety of acrylonitrile butadiene styrenes (ABS plastic) as a colorant. When ground down to an average diameter of slightly less than 1 micrometer, ABS plastics create tattoo pigments that are less likely to fade or blur over time than the traditional pigments. The tattoo dye can also contain non colorants, including but not limited to arsenic, cadmium, lead, nickel, antimony, chromium and cobalt. Common ingredients of red-coloured inks are mercury and cadmium; yellow-coloured inks commonly contain lead, cadmium and zinc. Orange-coloured inks usually cadmium. Common ingredients of green-coloured inks are lead, chromium and copper; and white inks commonly contain lead, zinc and barium.

According to FDA Consumer Health Information, "Think Before You Ink: Are Tattoos Safe?" (October 2009), No tattoo pigments are FDA approved; some are even repurposed printer inks and pigments suitable for automobile paint. "Removal is time-consuming, costly, and doesn't always work." FDA warns: do not buy or order online do-it-yourself tattoo removal products. These acid-based products are not FDA-approved and can cause bad skin reactions."

Seldom are any FDA-approved dyes used for tattoos. At best, the dye may be approved for cosmetic use—a surface application, not an injection. A variety of serious, even life threatening problems have been reported. In Europe many of the azo pigments, such as red PR 22, are not even allowed in cosmetics since they frequently react to produce carcinogenic compounds. The use of mercury, cadmium and other heavy metals can cause poisoning. Other case reports have disclosed cutaneous pseudolymphoma, granulomatous reaction, allergic reactions, pseudodepitheliomalous epidermal hyperplasia and even skin cancer.

The most common method of tattooing utilizes an electric tattoo machine, which inserts ink into the skin via a group of needles that are attached to an oscillating unit. The unit rapidly and repeatedly drives the needles in and out of the skin, usually 80 to 150 times a second. A small tattoo of simple design might take fifteen minutes to complete; whereas, a more elaborate design may require multiple, lengthy sessions.

Recently, cosmetic tattoos have become increasingly popular for adorning eyebrows and eyelids and have greatly expanded the market. It is estimated that as many as 4 in 10 citizens in the US have at least one tattoo. With such increased popularity comes an increased need for tattoo removal. Many of these tattooed individuals (reportedly ranging from about 14-21% of tattoo wearers) at some point wish to have their tattoo removed for one of many reasons. Sometimes there are medical reasons: Amateur tattoos may result in mercury poisoning; allergies to ink may arise. Many more are personal reasons. For example, an individual may have impulsively gotten a tattoo and now regrets that decision. Alternatively, a change in life circumstances may motivate the desire to have a tattoo removed. For example, an individual tattooed with the name or image of a spouse or lover may become estranged from that individual. Even if a tattooed individual desires to keep a tattoo, outside influence may motivate the decision to have it removed. A tattoo in an area of the body not covered by clothing such as the face, neck, hands or lower arms may make securing employment in certain professions more difficult. People leaving gangs often want to have their gang tattoos removed, to avoid confrontations with their former gang members and opposing gangs.

Current treatment options for tattoo removal include a variety of lasers, dermabrasion, salabrasion (abrasion with salt), surgical excision, cryotherapy and tattoo removal topical creams and lotions. Do-it-yourself topical creams cannot penetrate the epidermis to the layer with tattoo pigments embedded in cells, so how they work is not clear; they require frequent, even daily applications over weeks and months and often no change is seen. Some treatments may be effective; they may be expensive, time consuming, and painful. The more effective home treatments require dermabrasion with abrasive salty pastes that remove outer layers of skin in large patches. In some cases, such treatments also may result in cosmetically undesirable scarring.

One of the more effective tattoo removal treatments is a laser surgical technique in which the tattooed area is irradiated with a high-energy, pulsating laser beam. The tattoo ink pigments absorb a portion of the laser radiation. As a consequence, the pigment particles become sufficiently hot (and painful) that they decompose into smaller fragments. In the process, the cellular integrity of the surrounding dermal cells may be destroyed. A single laser treatment usually produces some fading of the tattoo because it sets up an immune reaction that drains some of the pigment fragments into the lymphatic system to reside in the lymph nodes; however, most pigment fragments become re-engulfed by still intact dermal cells and so remain visible. In nearly all cases, patients are not satisfied with the results of the first laser treatment, and they must return for numerous additional treatments. In the meantime, the laser has changed the color of some ink pigments, e.g., white or red to black, worsening the appearance for months. This change of color signals changes in the dye molecules and breaking of internal bonds into smaller molecules, some of which are toxic.

SUMMARY

In one embodiment, there is provided a method for treating a medical condition resulting from a tattoo that has the steps of cleaning at least one surface of the tattoo; preparing a plurality of needles to administer a formulation comprising a solution comprising aloe, less than 30% by weight salt, carboxymethylcellulose and distilled water; covering the surface of the tattoo and surrounding area with injections of the solution until the selected area has a different appearance; spreading the solution on the surface of the tattoo to provide a coating; and permitting the solution to dry.

Optionally, the formulation has less than about 30% by weight Himalayan salt, distilled water, carboxymethylcellulose and aloe vera. An additional step in the method is treating the tattooed area with an anesthetic introduced via cream before the skin is broken. Another optional step is injecting into tattoo area an anesthetic liquid. The step of permitting the solution to dry lasts at least 15 minutes. Alternately, the solution can be allowed to dry on the tattooed skin area for about 8-30 minutes.

In another embodiment, there is provided a tattoo removal formulation having water; less than 30% by weight salt; aloe; and carboxymethylcellulose. Preferably the salt is Himalayan salt. Preferably the aloe is aloe vera. Preferably the water is distilled water. Preferably, the salt is about 15-30% of the formulation. Preferably the water is about 50-95% of the formulation. Preferably the carboxymethylcellulose is about 0.2 to 10% of the formulation. Preferably the aloe is about 0.05 to 4% of the formulation. In another embodiment, the formulation can also contain bentonite, soy, turmeric or a combination thereof. In yet another embodiment, the formulation also has frankincense, sandalwood or a combination thereof. Optionally, alginate, gelatin, soy, or a combination can be added.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
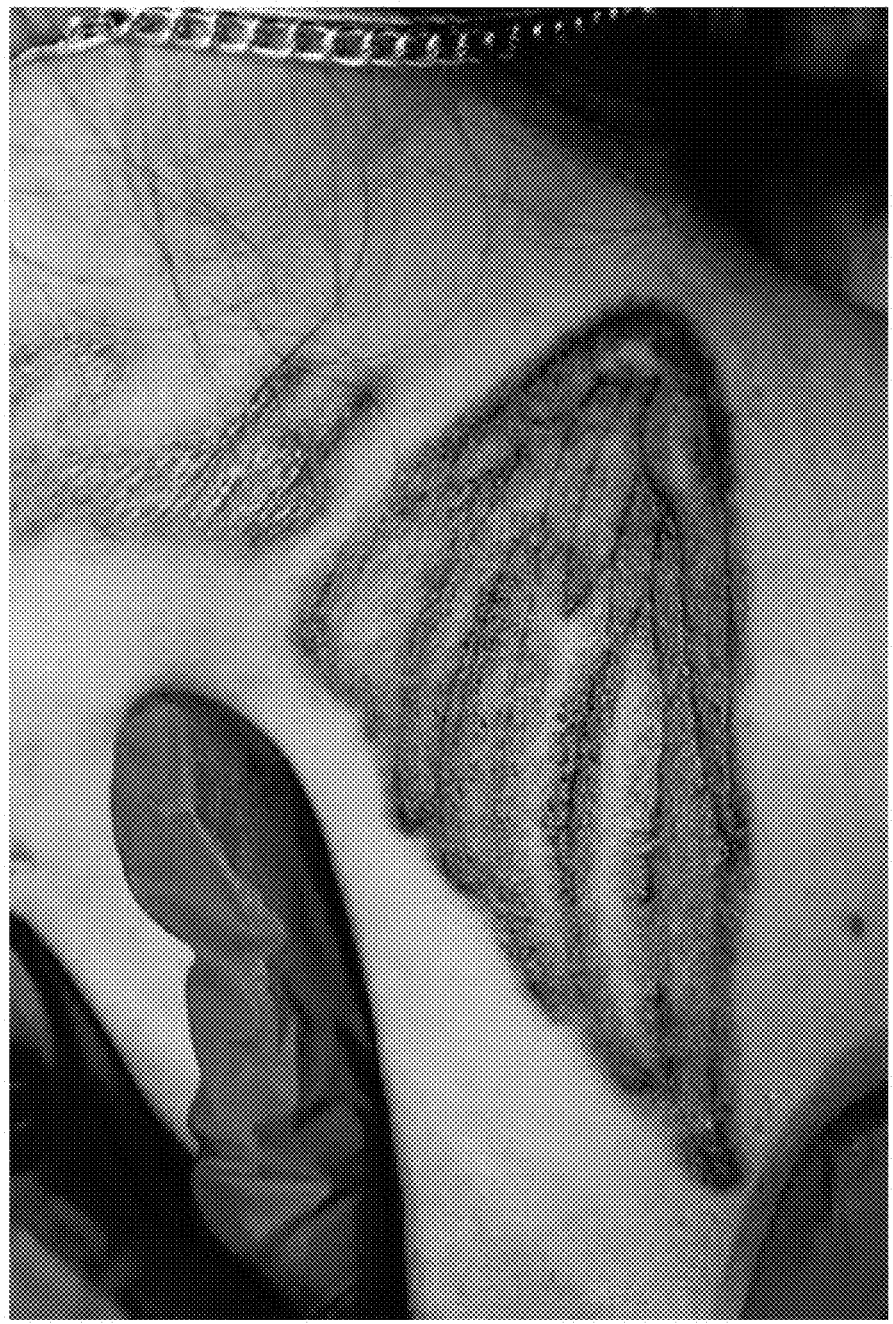
FIG. 1 is a photo of a partially treated tattoo with some of the tattoo looking darker and indicating optimal treatment.

We have observed a number of poor tattoo removals. We grew to believe that there is a need for a tattoo removal process that is safe (i.e., less damaging to the skin and removes the tattoo pigments from the body), pain free, efficient, economical and complete and does not subject the patient to excessive pain or discomfort. Existing treatments do not effectively and quickly remove tattoo dyes from the body: Merely rubbing a homemade mixture such as honey or lemon into the skin surface seldom has an effect, even after months of daily application and rubbing. We have also found that tattoos with the newer ABS plastic pigment dyes are even harder to affect with do-it-yourself treatments, which at best lighten traditional dyes, but not these dyes. Rubbing salt pastes onto the skin abrades continuous areas of skin. Abrading such areas of the skin results in the loss of epidermis which slowly grows in from the edges of the abraded patch. Large abraded areas often result in scarring, which interfere with obtaining the desired esthetic effect.

We identified shortcomings with the current laser treatments that break up the dye but rely on the slow, relatively passive lymphatic system to gradually transport pigment granules to lymph nodes; further dye removal from the body is unknown. When a tattooed individual has an allergic reaction to a dye or is poisoned by a dye containing mercury or other deleterious poisons, laser treatment breaks up the clumps of dye and spreads the dye through the body, contributing to a more severe reaction than was already experienced. The laser has been proven to break up the popular azo dyes into toxic compounds.

We also saw a method utilizing tattoo equipment to inject a mixture that was 80% salt with only a minor amount of water. Such a high salt concentration not only is extremely painful but also needs to be performed on relatively small areas of skin, or else the electrolyte balance of the body would suffer. Thus, such a method would have deleterious consequences when large areas are treated to remove poison dyes or dyes causing allergic reactions. Our inventive solution has less than about 30% salt which is highly effective in drawing body fluid into the treated area where together the injected solution and body fluids help transport the tattoo dye to the surface through the small channels created by the needles. We have seen our inventive method draw out not only the dyes but inflammation and/or infection caused by the dyes (see Examples).

The present invention provides an improved formulation and method for removing tattoos. Our new method is a non-laser tattoo removal method that promptly removes the ink from the body, minimizes discomfort, minimizes scarring and requires fewer treatments than laser. Our new method is superior to other methods using dermabrasion, because we employ a plurality of needles, such as provided in an electrical tattooing machine, to introduce the inventive solution directly to the location of the tattoo dye. The needles open small channels to drain the extra concentrated fluid and dye. Use of multiple small needles means that most of the epidermis is left intact, except for punctures. The remaining epidermis can protect the underlying dermis cells and provide a structure for skin cell replacement that does not require the longer growth period of skin cells from the edges of a dermabraded area. Thus, we have experienced no or only slight scarring due to this inventive method.

Another advantage of the inventive method is that tattoo dye starts leaving the skin immediately upon the start of the application of needles, and continues afterward as the inventive solution dries over the treated area and forms a scab; clients reported seeing a reverse of their tattoos on the underside of the scab. This is particularly beneficial in individuals who have been poisoned by tattoo dye or experience an allergic reaction. The dye causing their poisoning and/or other reaction begins to leave the body even during treatment; recovery begins right away.

The method of the present invention may be performed to remove a mature or recent tattoo. A mature tattoo is defined herein as a tattoo in which most of the tattoo ink pigment particles have been engulfed by, and reside in the cytoplasm of, dermal cells such as, for example, macrophages and fibroblasts. Alternatively, the method of the present invention may be performed to remove freshly applied or immature tattoos. A freshly applied or immature tattoo may be less than one week old, for example, 24-72 hours old. In a freshly applied tattoo or an immature tattoo, a majority of the tattoo ink pigment particles remain free in the interstitial space between dermal cells. Microscopic analysis of skin with freshly applied tattoos shows that the tattoo ink pigment particles remain in the free extracellular space of the dermal cells for several days before the pigment particles are engulfed by macrophages and/or fibroblast cells.

The first steps in the preparation process of the present invention involve sterilizing the tattooed area. For sterilizing the tattooed area, we used a standard disinfectant such as an antibacterial soap or isopropyl alcohol. The cleaned tattooed area is preferably treated with a topical anesthetic such as lidocaine to minimize discomfort during the process. Creams are preferred to maintain the surface of the epidermis.

Next, using standard tattoo needles or preferably a standard tattoo machine, the skin in the tattooed area is pierced to access the layer of ink using light pressure. In the preferred embodiment, a large "shader" tattoo needle such as a 14 Round is used to minimize discomfort and prevent scarring. A topical anesthetic may be introduced via cream prior to opening the skin, and via liquid after opening the skin. It is preferable to apply the anesthetic at least several minutes before opening the skin. The entirety of the skin covering the tattooed area is treated in this manner to allow access to all tattoo ink to be removed. Once the tattooed area has been opened in this manner, the tattooed area is cleaned with water and/or an anesthetic liquid.

The next step is to apply a thin layer of the formulation of the present invention to the tattooed area in an amount to cover the opened skin. In the preferred embodiment of the present invention, the formulation is a special and unique combination of the following ingredients: Himalayan salt, distilled water, carboxymethylcellulose and aloe vera. This specialized combination of ingredients leads to an advanced removal process, allowing a more beneficial result over traditional methods.

Although different types of salt (sodium chloride) were tried and can be used, we found the best results with Himalayan salt. Water should be purified to minimize the possibility of infection. Aloe vera helps with the healing process. In a preferred embodiment, salt is about 15% to about 30%, carboxymethylcellulose is about 0.2% to about 10%, aloe is about 0.05% to about 4.0% (preferably *Aloe Barbadensis* concentrated 200 to 1) and purified water is about 60% to 95%. In a preferred embodiment, sodium chloride comprises 10-30% and more preferably about 20% to 27%. In a preferred embodiment, the content of carboxymethylcellulose is about 0.5% to about 3% and more preferably about 0.8% to about 2%. In a preferred embodiment, the content of aloe is about 0.1% to about 0.5% and more preferably about 0.2% to about 0.4%. In a preferred embodiment, water is about 65% to about 85%, and more preferably about 70% to about 82%.

It should be realized that the above ingredients can be added in various percentages so long as the mixture provides a higher level of salt to encourage swelling in the applied area. As will be understood by one of ordinary skill in the art, the formulation will not lose its efficacy as a result of slight variations made to the relative weights of the ingredients.

Besides sodium chloride, other electrolytes can be used in the inventive solution. These include but are not limited to potassium chloride, sodium carbonate, sodium bicarbonate, magnesium chloride, magnesium glycinate, calcium chloride, calcium carbonate, Dead Sea salt and combinations thereof. One source of Himalayan salt is mined in Pakistan by Pakistan Minerals Development Corporation and sold by Gamma Salt Cristals Ltd. of Toronto, Ontario under the trade-mark GAMMA and product name GAMMA Genuine Himalayan Crystal Salt. The chemical composition of the GAMMA Genuine Himalayan Crystal Salt according to a certificate issued by DM Brothers Importers and Exporters of Lahore, Pakistan is 98.86% sodium chloride, 0.25% sodium sulphate, 0.63% calcium magnesium, 0.04% water and 0.1% insoluble material.

Sea salt is a generic term for salt prepared from sea or ocean-water ponds from which the water evaporates, gradually raising the salt concentration. The most common elements tend to be sodium chloride (e.g., 85.62%) and other ions, mainly magnesium, sulfate, potassium, bicarbonate, calcium, bromide, fluoride and strontium. A wealth of trace elements are also present, including iron, copper, manganese, phosphorus, silicon, and nitrogen.

The composition varies from common table salt which has been purified to include only sodium chloride (98%+) and small amounts of an anti-clumping agent (often hexacyanoferrate) and iodine. Himalayan salt does not need an anti-clumping agent when it is purchased as salt crystals that are ground by purchaser.

Besides carboxymethylcellulose, other binding chemicals include but are not limited to magnesium aluminum silicate, starch paste, alginate, gelatin, tragacanth, sodium methylcellulose, polyvinylpyrrolidone, sucrose, acacia or a combination thereof. Carboxymethylcellulose also serves as a suspending agent for the inventive solution, and other suspending agents include but are not limited to magnesium aluminum silicate, starch paste, gelatin, tragacanth, methylcellulose, polyvinylpyrrolidone, dextran 40, dextran 70, lanolin, glycerine, petrolatum, polyethylene glycol, polyvinyl alcohol, ethoxylated isostearly alcohols, polyoxyethylene sorbitol, sorbitan esters, microcrystalline cellulose, aluminum metahydroxide, bentonite, agar-agar, Polyacrylic acid, magnesium aluminum silicate, xanthan gum, hyaluronic acid, guar gum, pectin fruit, gallan gum, locust bean gum and psyllium and a combination thereof.

Aloe is a well respected botanical herb, used in cosmetics and medicines. In topical uses, it is considered to have a soothing, moisturizing effect and has enjoyed long use in burn and abrasion treatment. It is obtained from any of a variety of aloe species, often as a viscous sap. In traditional medicine, a leaf is broken off and rubbed on an affected area. Preferred are *ale barbadensis, aloe barbadensis* extract and *aloe barbadensis* gel. Certified organic aloe vera powder (95%) is commercially available under the trademark SC200X™ and is hydrated in a mixing tank, to which other materials like agar (0.2%) can be added. The mixture can be pasteurized by heating to 160° F. for about 30 min.

Other botanical extracts that may help in healing include but are not limited to green tea, soy, milk thistle, algae, angelica, bitter orange, coffee, goldthread, grapefruit, hoellen, honeysuckle, Job's tears, lithospermum, mulberry, peony, puerarua, arnica mountana extract, apricot (*prunus armeniaca*) kernel oil, safflower and combinations thereof. Soy in particular contains a relatively high level of Phytic acid, which is an antioxidant and acts as a chelating agent. Chelating agents can help detoxify the body of toxic heavy metals, which some tattoo dyes contain and which may be converted to a chemically inert form for easier removal. As for angelica, the boiled roots have been used to treat wounds, both internally and externally.

There are other optional ingredients that can be added to the treatment serum and/or applied afterward. Chief among these are clay (preferably bentonite), sandalwood, turmeric and frankincense.

Medicinal clay can help absorb fluids and electrolytes and other charged species, and as such is capable of aiding the removal of swelling and unwanted ink from a tattoo. A frequently used name is bentonite, although it is the official name for aluminum phyllosilicate clay consisting mostly of montmorillonite. There are different types with predominantly potassium, sodium, calcium and aluminum cations. Sometimes the amount of a cation is adjusted by substitution with a different cation to adjust the clay's properties. For example, sodium bentonite may absorb several times its weight in water, and calcium bentonite absorbs electrolytes in solutions. When the two types of bentonites are combined, the result is a combination with both excellent water and ion absorption. For ionized tattoo dyes, this is a particularly useful combination. Bentonite has been used as a laxative and is also a base in some dermatologic formulas, such as a skin block to guard against poison ivy contact.

Frankincense is a traditional remedy that has been prized for aiding healthy skin, healing wounds and providing relief from stings such as scorpion stings, among other uses. As such, it can contribute to the healing of the treated tattoo. It is obtained from *Boswellia* trees, which are tapped for their sap and found mainly in the Middle East, central Africa and India. It is sometimes used in skin care products. The combination of frankincense and sandalwood was recently found to kill bladder cancer cells.

Sandalwood is available as an essential oil and chosen for its antiseptic/disinfectant, anti-inflammatory and astringent properties. Sandalwood contributes to healing of the treated site and more client comfort. Those benefit users with wound cleanliness. The essential oil is extracted from the wood of mature *Santalum* trees by steam distillation. As an antiseptic, it is said to protect wounds from developing infections. Its anti-inflammatory property includes a cooling effect and relief from insect bites. As an astringent it helps tighten skin which may assist in recovery. It also aids in healing skin and even scars and spots faster. When applied to raw skin, sandalwood is recommended for dilution in a carrier oil.

Turmeric is selected for its assistance in healing wounds. It has a reputation for antiseptic action and preventing bacterial infection of wounds, such as by *E. coli, Staphylococcus* and *bacillus*. These factors make turmeric an aid to healing after the inventive treatment. Its anti-inflammatory action can help relieve inflammation. It even has an analgesic action to relieve pain. Moreover it helps close wounds by enhancing new skin cells and can reduce scar formation. A prominent component of Turmeric is curcumin whose anti-inflammatory, antibacterial and anti-viral properties have been formally studies and found useful in many conditions. Turmeric is a popular herb of the ginger family.

Moisturizing agents may be added to the inventive formulation or utilized after the initial treatment and healing phase. Examples of moisturizing agents include but are not limited to amino acids, chondroitin sulphate, diglycerin, erythritol, fructose, glucose, glycerine, glycerol polymers, glycol, 1,2,6-hexanetriol, honey, hyaluronic acid, hydrogenated honey, hydrogenated starch hydrolysage, inositol, lactitol, maltitol, maltose, mannitol, natural moisturizing factor, PEG-15, butanediol, polyglyceryl sorbitol, salts of pyrollidone carboxylic acid, potassium PCA, propylene glycol, sodium glucuronate, sodium PCA, sorbitol, cucrose, trehalose, urea, xylitol, acetylated lanolin, acetylated lanolin alcohol, acrylates with C10-30 alkyl acrylate crosspolymer, acrylates copolymer, alanine, algae extract, althea officinalis extract, aluminium starch octenyl succinate, aluminium stearate, arginine aspartate, ascorbic acid and combinations thereof.

Once applied, the formulation is preferably allowed to sit on the tattooed area for at least about 12 minutes to allow for treatment of the tattoo ink. Then, any excess formulation may be removed from the tattooed area using a sterile applicator such as gauze. Most of the formulation is intended to remain on the treated area until it dries into a scab and falls off of its own accord.

For some time after application, the tattooed area appears swollen and red as a result of the procedure. The treated area should be guarded, particularly until it dries as a scab. Once the scab has formed, the area can be covered with a non-stick dressing, particularly if it is under clothing. Approximately 24-48 hours following treatment, a scab will form over the tattooed area, allowing exfoliation of the tattoo ink. The scab protects the area and draws out the unwanted ink into the scab over the following one to three weeks. Depending on a variety of factors such as the location of the tattooed area, the patient's natural skin pigment and the ink used in the tattoo to be removed, repeated treatments may be necessary.

EXAMPLE 1

One embodiment of the inventive procedure begins with the technician organizing all materials needed on a tray convenient to the client. And then draping and preparing a tattooing machine (optional) with the single-use parts: a set of needles, grommet, and tube. The technician inserts the tube into the optional machine and then the needle(s) while wearing sterile gloves, the tube is inserted into the machine and the needle set is inserted into the tube attached to the tubing. The needle(s) should only protrude 1.5 mm from the tube.

The technician then gloves and cleans the client's tattoo area with a disinfectant wipe. Preferably the client shall have applied an anesthetic as much as two hours prior to the procedure to reduce pain from the punctures. The technician may apply anesthetic to the working area during the procedure by picking up anesthetic with the needle(s) and applying to the surface and into the skin.

The technician and/or machine causes the needle(s) to move quickly in and out of the tubing, repeating some of the action of getting a tattoo, with which clients are already familiar. Numerous 1.5 mm punctures are made completely over the chosen area, resulting in some bleeding which should be frequently removed with clean gauze wipes. The technician proceeds until the entire area is fully treated, reapplying anesthetic as needed. One way to judge the completeness of the treatment is to inspect and see whether the underlying tattoo has become markedly more noticeable, which indicates the ink layer is in better contact with the surface. See FIG. 1, a photo of a partially treated tattoo with some of the tattoo looking darker and indicating optimal treatment.

Once the initial step has been completed, the next step is application of the inventive solution to the entire treated surface in a thin layer. Thirdly, the solution is lightly tattooed into the treated area. Any drips are removed with gauze. The client must remain stationary for at least 12 minutes. Any drips not on the treated area are removed and the surrounding area is thoroughly cleaned with water. At this point the treated area is red and swollen; the swelling means there is extra fluid in the area to help in the ink removal.

These three steps are only the beginning of the tattoo removal process. The inventive solution dries in place, forms a scab which absorbs the tattoo dye from the skin. That is why the client is instructed to leave the area open to air drying. A scab typically forms over 1-3 days. It is important to leave the scab alone until it falls off in two to three weeks. We have observed many scabs and they have noticeable tattoo dye in them—sometimes even a relief of the tattoo pattern.

Interestingly, it is very important to keep the scab dry until it falls off, because we occasionally observe a failure of the process and it often follows the scab having gotten wet.

After the scab falls off, the skin is generally light pink and scarring is minimized. Because the contact with the skin was through many small holes, most of the skin was left in place and there is rapid healing of the intact area into the numerous tiny puncture holes. This contrasts with previous methods that are capable of burning larger areas of skin (laser), or that remove patches of skin, sometimes requiring skin transplant.

Of course, the pink healing skin requires sun protection or it develops new pigmentation on its own. Keeping the pink, healing skin out of the sun for a year allows complete healing.

Depending on the history of the tattoo and its treatment, more than one procedure may be necessary to obtain the client's desired esthetic effect. Tattoos that were heavily inked or applied more than once to the site result in the deposit of more ink that may take longer to remove. Moreover, previous procedures to remove the tattoo may cause scarring in the affected area that may take more time to overcome with additional inventive procedures. In addition, clients picking at the edges of the scab or removing the scab prematurely decrease the time of contact with the tattoo and may diminish the amount of dye removed.

This procedure has been performed successfully on many clients. Following are descriptions of cases and photos.

EXAMPLE 2

A previously healthy, professional male athlete had travelled to Thailand and obtained large tattoos on the arms and back from a traditional healer. Upon his return to his home, he developed several symptoms including joint pain and weakness in his muscles, which a physician diagnosed as mercury poisoning, with particularly high laboratory values, and attributed to the tattoos. His doctor researched tattoo removal methods, and recommended excision of the tattoos and skin grafting. In the meantime the male heard of this inventive method. After one inventive treatment he started to feel much better and returned to an active lifestyle. Within several months he was able to resume his professional career.

EXAMPLE 3

Figure 2A:
FIGS. 2A and 2B are before and after photos of an initially inflamed and swollen tattoo and the later healing diminished coloration with no swelling or inflammation.
Figure 2B:
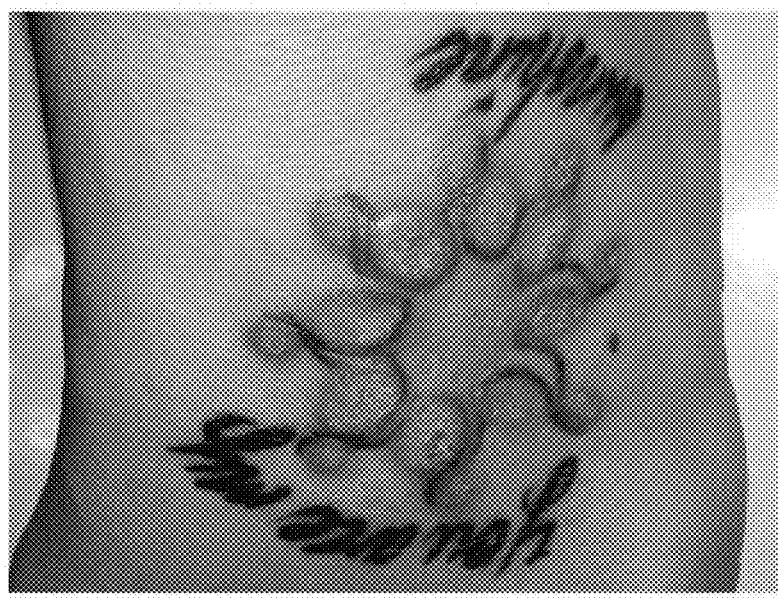

A female developed an allergy to her tattoo, probably to the red pigment. The tattooed area was itchy, swollen and appeared infected (FIG. 2A). A laser tattoo removal professional refused to treat her, fearing that the infection might spread and treatment would break up the pigments and permit them to spread in her body, causing a more severe reaction. She underwent the inventive treatment that lifted much of the dyes into her scab. She took longer to heal than normal and the area remained itchy; the infection had dissipated (FIG. 2B). She reported feeling much better and put off additional treatments for at least several months.

EXAMPLE 4

Figures 3A, 3B:
FIGS. 3A and 3B are before and after photos of a swollen and inflamed red tattoo and a later area with less tattoo color and no inflammation of swelling.

A female client sought treatment for her red dye tattoo that was swollen and infected FIG. 3A). During treatment the infected red ink oozed out of the skin. In an after photo (FIG. 3B), the tattoo had lightened significantly and was no longer itchy or appearing infected. Client planned another follow-up treatment to remove more of the red ink.

EXAMPLE 5

Figure 4A:
FIGS. 4A and 4B are before and after photos of permanent make up removal with one treatment.
Figure 4B:
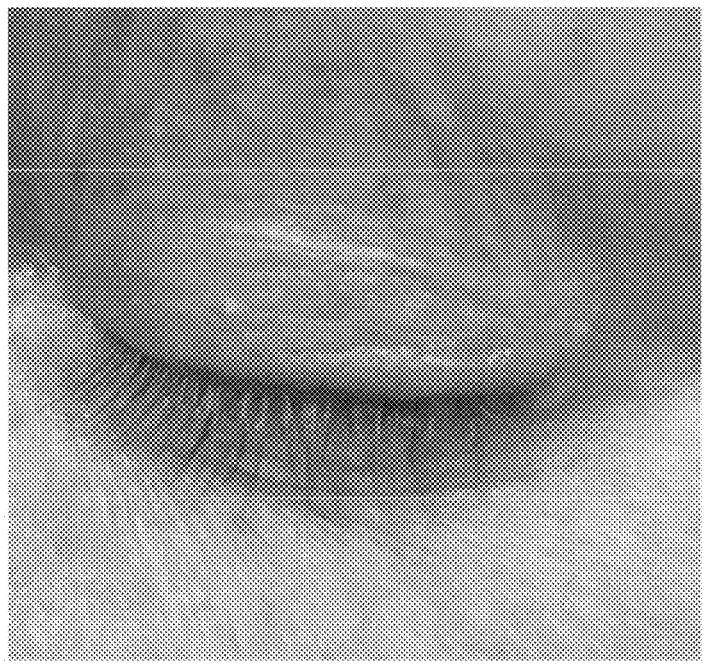

A 62-year-old female had a blue tattoo at the edge of her upper eyelid ("permanent makeup") that she wanted removed. She had no prior laser treatment. FIGS. 4A and 4B, respectively, show her eyelid before the inventive treatment and after only one treatment, with virtually no remaining color.

EXAMPLE 6

Figure 5A:
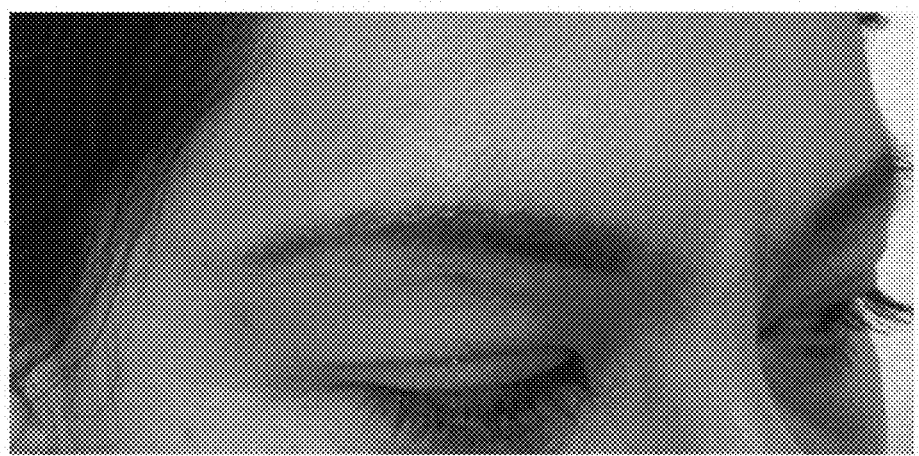
FIGS. 5A and 5B are before and after photos of permanent make up removal.
Figure 5B:

A 31-year-old female had dark brown permanent makeup on her eyebrow and wanted it removed. She had not tried laser treatment. FIGS. 5A and 5B, respectively, show her eyebrow before and after the inventive treatment (one session).

EXAMPLE 7

Figure 6A:
FIGS. 6A and 6B are before and after photos of a tattoo after four inventive treatments.
Figure 6B:
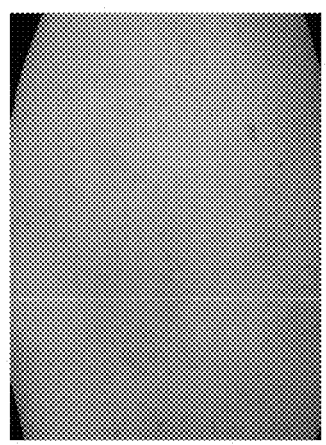

A 56-year-old male had a 12-inch square tattoo that was treated with the inventive treatment. He had no prior laser treatments. FIGS. 6A and 6B, respectively, show the skin before and after treatment in four sessions. FIG. 6B shows only the pink skin recovering from the treatment. We have found that the skin regains its natural appearance over time.

EXAMPLE 8

Figure 7A:
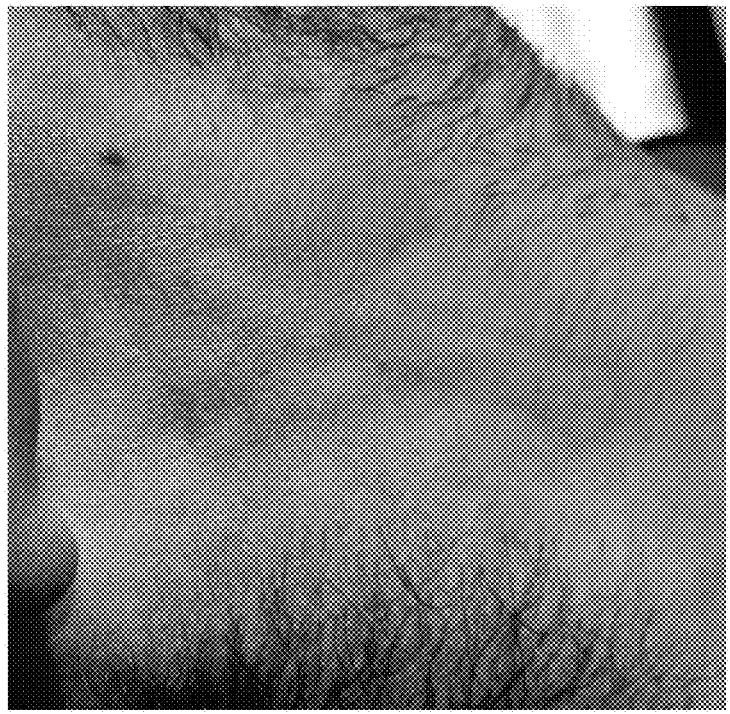
FIGS. 7A and 7B are before and after photos of a tattoo that had previously received seven laser treatments and after a single inventive treatment.
Figure 7B:

A 23-year-old male had gotten a one-inch-square tattoo below and behind his ear. After seven laser treatments, he still had a noticeable dark shadow (FIG. 7A). After one session of the inventive treatment, the darkness was gone and his skin had a healthy pink appearance (FIG. 7B).

EXAMPLE 9

Figure 8B:
FIGS. 8A and 8B are before and after photos of a tattoo previously receiving three laser treatments and after a single inventive treatment.
Figure 8A:

Male client ON had received three laser treatments in an attempt to remove his tattoo, which remained a grey color and is shown in FIG. 8A. FIG. 8B shows the result after one inventive treatment. The skin in the area of the tattoo is now pink and no ink is visible.

EXAMPLE 10

Figure 9A:
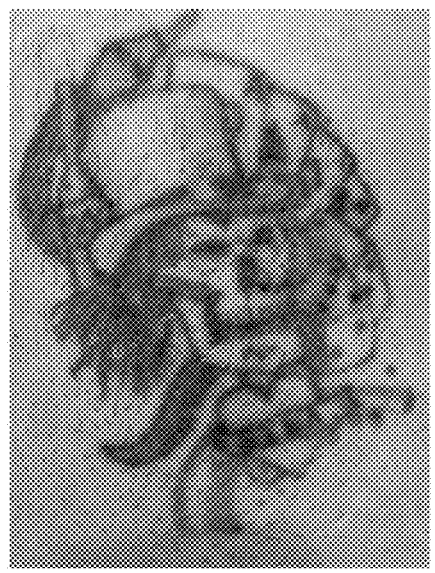
FIGS. 9A-9D show a dual tattoo, of which the lower portion was subsequently treated three times, respectively FIGS. 7B, 7C and 7D. By the third inventive treatment, no dye could be seen in the lower portion but the upper portion remained intact as desired.
Figure 9B:
Figure 9C:
Figure 9D:
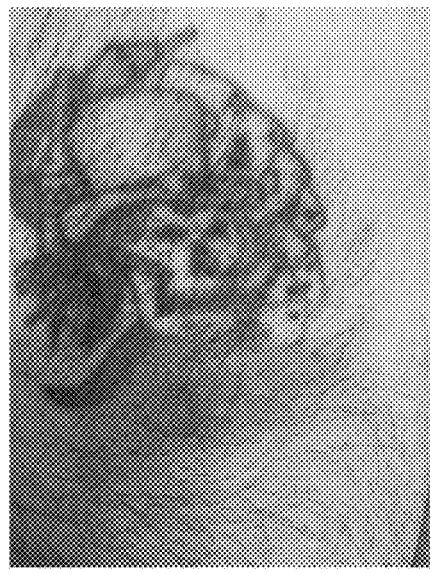

Male client HE had received a skull tattoo with a heart underneath encircling his girlfriend's name, as shown in FIG. 9A. He wanted to keep the skull tattoo but remove the heart and name. After one treatment the heart tattoo was lighter and the skin pink (FIG. 9B). After a second treatment, the tattoo was even lighter (FIG. 9C). After the third treatment no ink was visible (FIG. 9D).

EXAMPLE 11

Figure 10A:
FIGS. 10A and 10B are before and after photos of a finger tattoo that had previously received five laser treatments and the after photo showing the removal or residual ink with one inventive treatment.
Figure 10B:
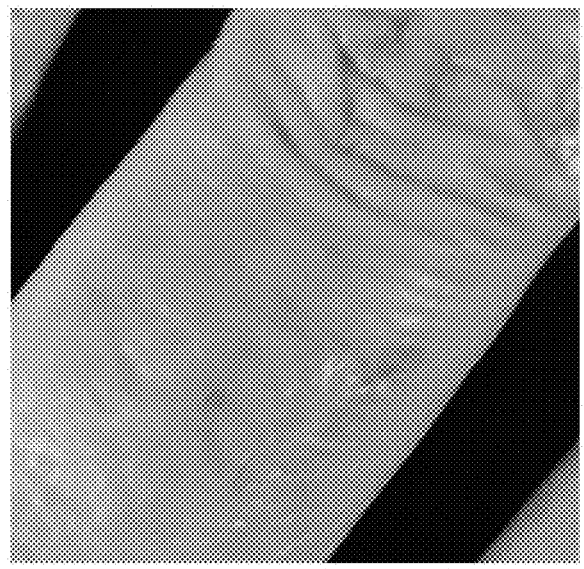

Female client JA had gotten a tattoo on a finger which had received five laser treatments but still had noticeable ink (FIG. 10A). The tattoo received two inventive treatments, which on close-up did not show any ink but the skin was pink (FIG. 10B).

EXAMPLE 12

Figure 11B:
FIGS. 11A and 11B are before and after photos of an eight-year-old tattoo receiving only a single inventive treatment.
Figure 11A:

Female client LI had her tattoo for seven years before undertaking the inventive treatment. Her tattoo (FIG. 11A) was much improved by a single inventive treatment as shown in FIG. 11B.

EXAMPLE 13

Client DL received a tattoo as a gift for his 50$^{th}$ birthday. However, he was unhappy with it and grew concerned with the ingredients of the ink. He sought the inventive treatment to remove his tattoo, and reported being happy with his new tattoo-free state after four treatments.

EXAMPLE 14

Client G had given herself two "tick and poke" tattoos and grew to regret their appearance and became embarrassed to show the tattoos in public. She knew she could not afford laser removal and feared the attendant pain. She was surprised by the amount of ink that could be taken out in five treatments, significantly fading both tattoos. She was pleased at the savings compared to laser treatment.

EXAMPLE 15

Client JB had obtained a matching tattoo on his palm with his now-ex-girlfriend. With the end of the relationship, he wanted to have the tattoo removed as fast, inexpensively and painlessly as possible. He reported that three treatments were sufficient to remove most of the ink and that the treatments were not painful.

EXAMPLE 16

Client LW had gotten many tattoos that covered her whole back. She wanted to be rid of them for many years and had tried "everything," including laser several times to no avail. She has been receiving the instant treatments for several months and expects to undergo more. "The results have been wonderful," and with the topical anesthetic, basically pain free.

EXAMPLE 17

Figure 12A:
FIGS. 12A-12H are before, interim and after photos that show the significant difference in ink in a treated tattoo, compared to the undisturbed adjacent tattoo.
Figure 12B:
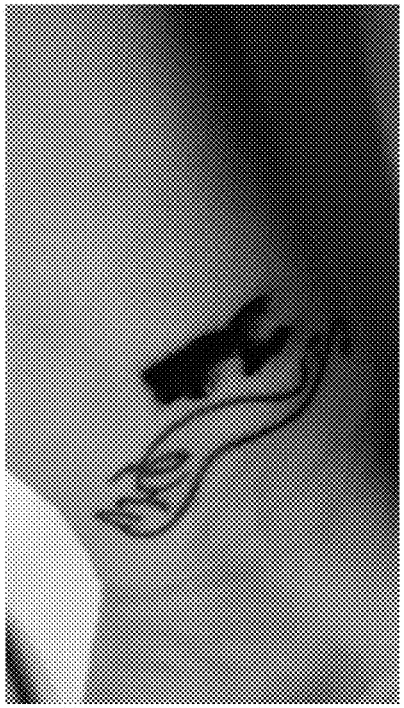
Figure 12C:
Figure 12D:
Figure 12F:
Figure 12H:
Figure 12E:
Figure 12G:
Figure 13A:
FIGS. 13A-13C are before, interim and after photos that show that the procedure is highly selective for only portions of a tattoo.
Figure 13B:
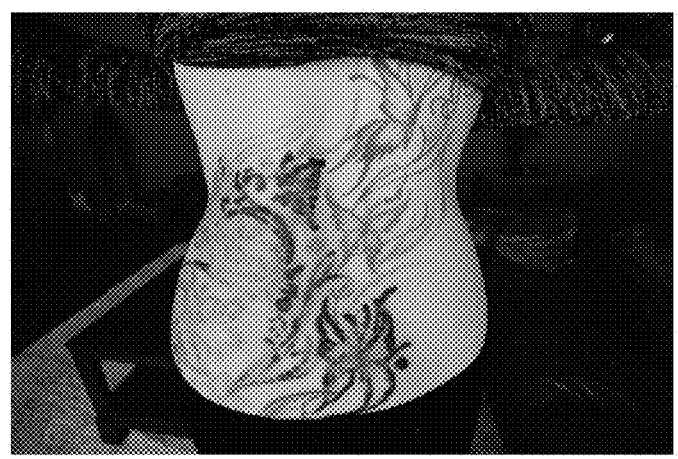
Figure 13C:
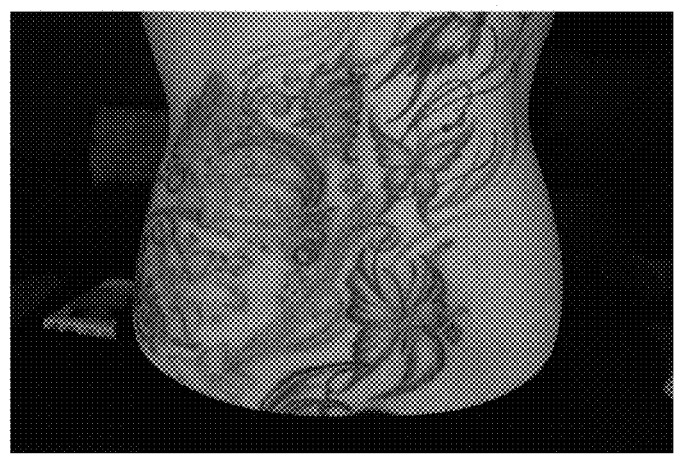

A female client had numerous tattoos and started the instant treatment on her wrist (FIGS. 12A-12D). FIG. 12A shows her wrist with a free form design and a name underneath, the latter to be removed. FIGS. 12B-12F show the treated name with a scab over it to withdraw tattoo ink over time. FIG. 12G shows the edge of the scab loosening. FIG. 12H shows the recovering skin with markedly reduced ink in the name compared to the free form tattoo which started with the same amount of ink. The client was so pleased with the results she requested additional treatment on her tattooed back shown in FIGS. 13A-13C. FIG. 13A shows the tattoo before treatment, FIG. 13B shows the tattoo highlighted by the application of tattoo needles, and FIG. 13C shows the healing back with the specific treated portion markedly reduced in ink.

EXAMPLE 18

Figure 14A:
FIGS. 14A-14B show a tattoo after laser treatment but before inventive treatment and the markedly reduced tattoo after the inventive treatment.
Figure 14B:

After trying one laser treatment, client ME requested the inventive treatment for a large tattoo on the back of her neck (FIG. 14A) which had been only partially reduced. FIG. 14B shows the dramatic reduction in ink in only one inventive treatment.

EXAMPLE 19

Figure 15B:
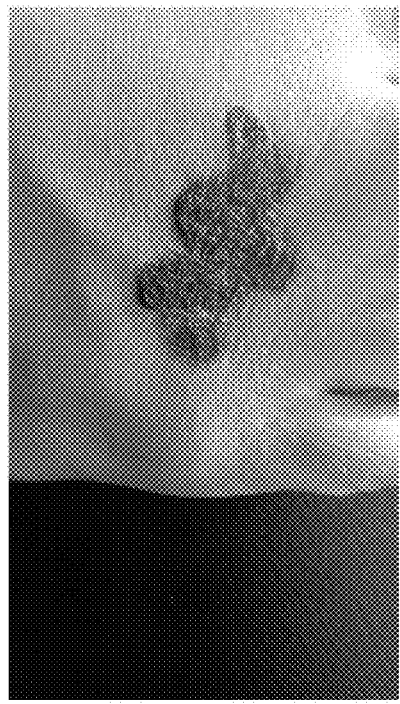
FIGS. 15A-15D show the stages of scabbing, scab peeling and healing of a tattoo previously partially treated with a laser.
Figure 15D:
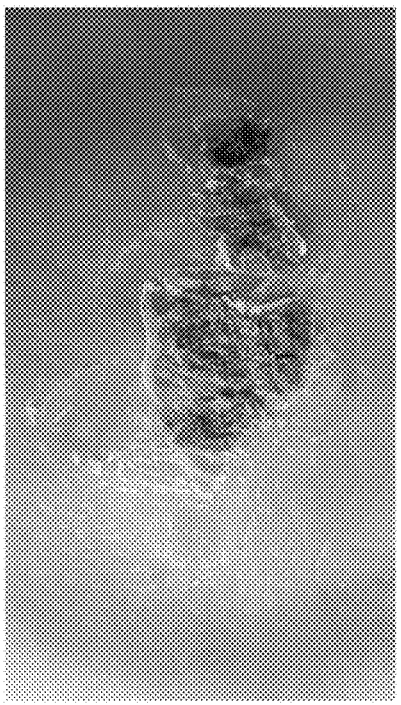
Figure 15A:
Figure 15C:

Client SA had tried one laser treatment on her "Playboy" tattoo with the result shown in FIG. 15A. After one inventive treatment, the initial scab is shown in FIG. 15B and a mature, peeling scab is shown in FIG. 15C. The healing skin with markedly less ink is shown in FIG. 15D.

EXAMPLE 20

Figure 16A:
FIGS. 16A-16D show the inventive treatment producing a progressive decrease in ink of a tattoo previously treated by laser.
Figure 16B:
Figure 16C:
Figure 16D:
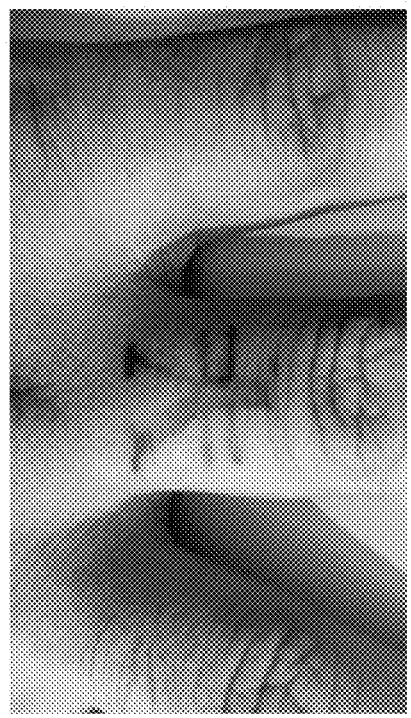

Client MI still needed to remove a tattoo—already laser treated thrice—from his finger, as shown in FIG. 16A. FIG. 16B shows the same finger treated with the inventive serum and beginning to scab. FIG. 16C shows the healing finger after one inventive treatment. After subsequent treatment with the inventive serum, the same finger gave up most of the ink (FIG. 16D).

EXAMPLE 21

Figure 17A:
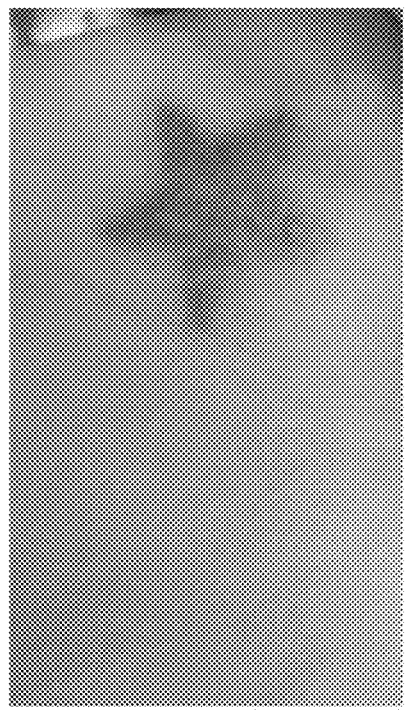
FIGS. 17A-17D show the inventive treatment producing a progressive decrease in ink of a tattoo previously treated by laser.
Figure 17B:
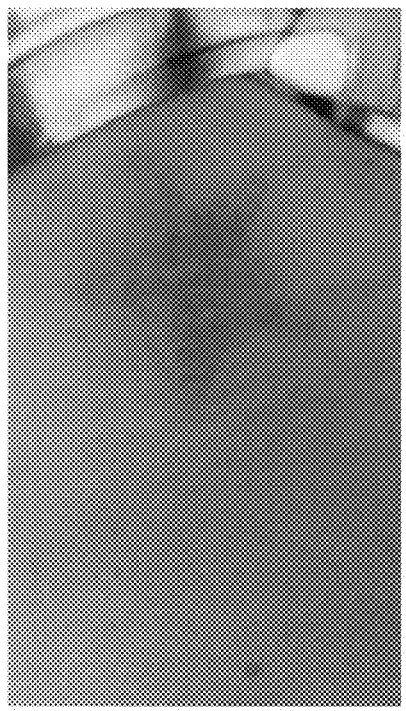
Figure 17C:
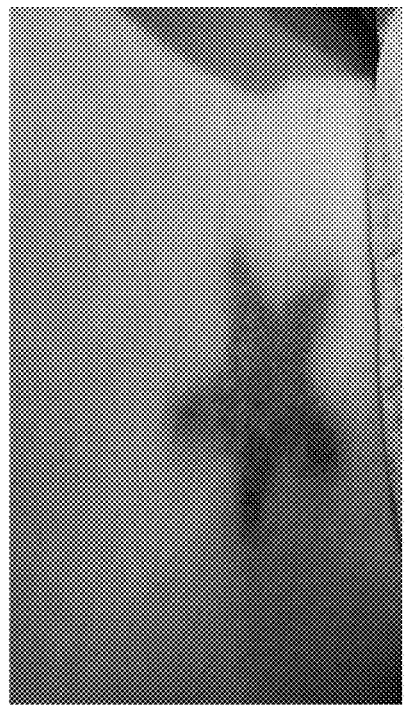
Figure 17D:
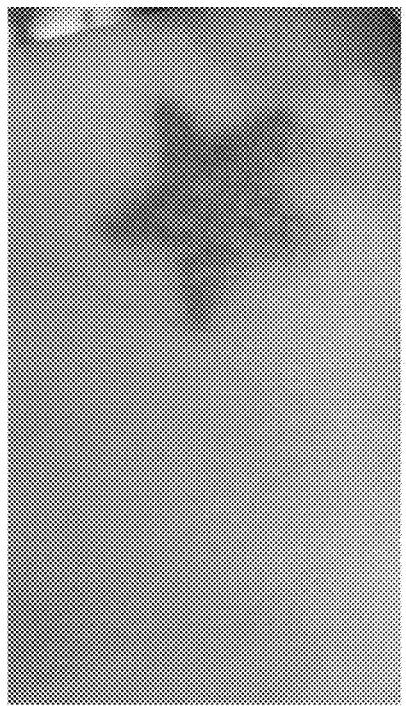

Client ST had four laser treatments to reduce the prominence of her star tattoo with the result shown in FIG. 17A. FIGS. 17B-17D show the fading tattoo after inventive treatments.

EXAMPLE 22

Figure 18A:
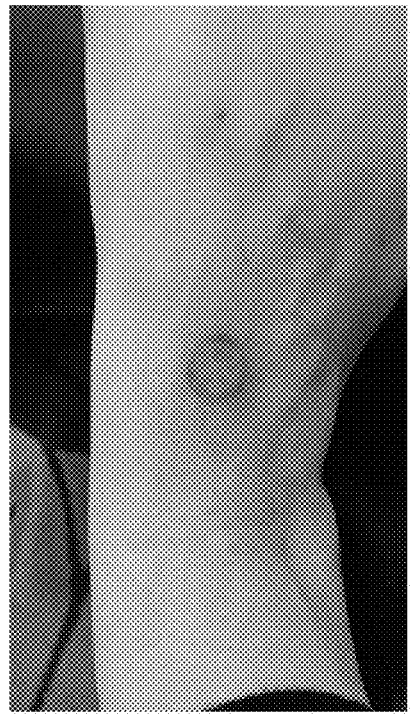
FIGS. 18A-18D show the inventive treatment producing a progressive decrease in ink of a tattoo.
Figure 18B:
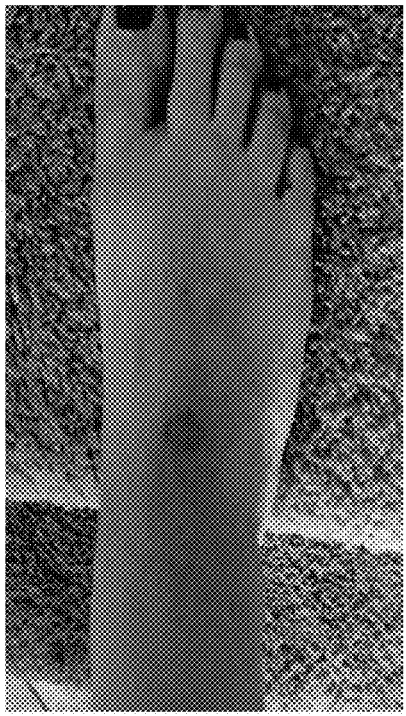
Figure 18C:
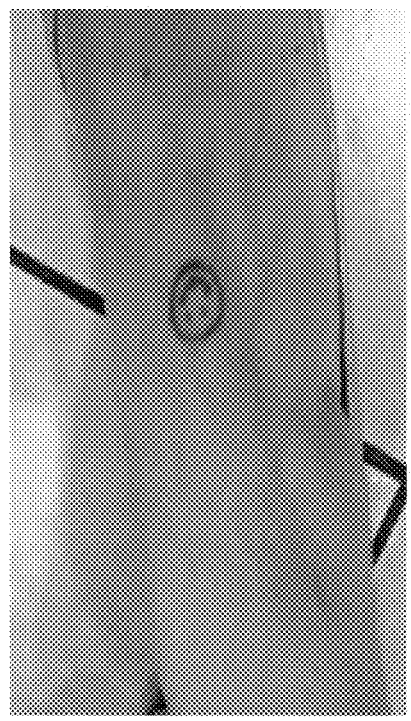
Figure 18D:
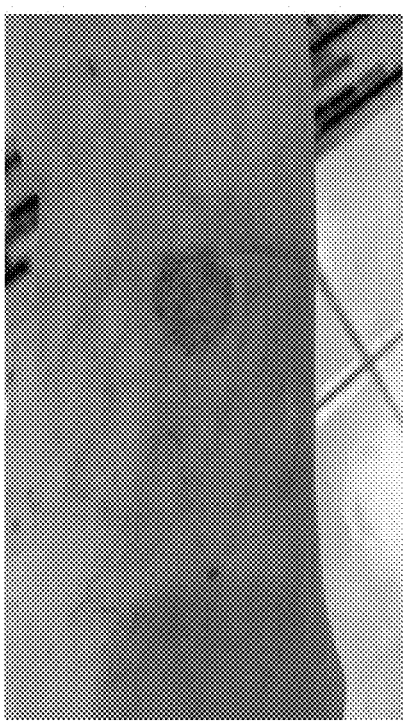

Client presented with a small tattoo on the front of her ankle (FIG. 18A). FIGS. 18B-18D show the tattoo receded after the inventive treatments.

EXAMPLE 23

Figure 19B:
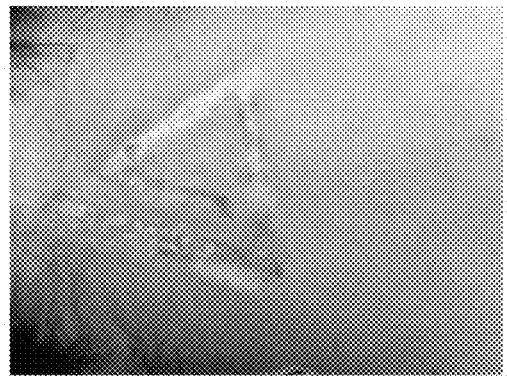
FIGS. 19A-19C show the before, interim and after photos of a prominent neck tattoo being reduced to a shadow.
Figure 19C:
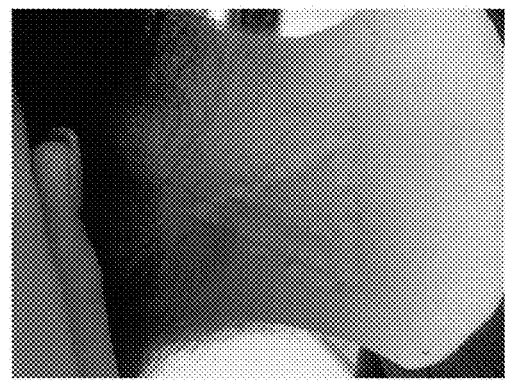
Figure 19A:
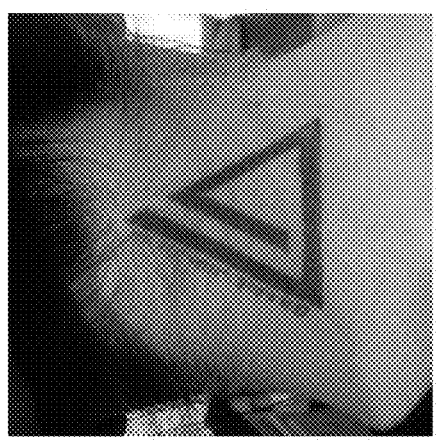

Client TR had a prominent untreated tattoo on her neck (FIG. 19A). FIG. 19B shows the tattoo after application of the inventive serum, and FIG. 19C shows the healing treatment area with a much diminished tattoo.

Following are additional exemplary formulas.

EXAMPLE 24

Another inventive formula includes Himalayan salt at 20-27%, aloe at 0.5-4%, carboxymethylcellulose 0.2-10%, soy at 0.5-3% and water at 45-93%.

EXAMPLE 25

Another inventive formula includes Himalayan salt at 20-28%, aloe at 0.5-4%, carboxymethylcellulose 0.2-10%, soy at 0.5-3% and water at 43-93%.

EXAMPLE 26

Another inventive formula includes Himalayan salt at 18-30%, aloe at 0.5-2%, carboxymethylcellulose 0.2-5%, soy at 0.5-3% and water at 43-93%. Alginate, gelatin, starch or a combination thereof are added at 0.3-5%.

EXAMPLE 27

Another inventive formula includes Himalayan salt at 20-30%, aloe at 0.2-2%, soy at 0.5-3% and distilled water at 50-90%. Alginate, gelatin, starch or a combination thereof are added at 0.3-5%.

EXAMPLE 28

Another inventive formula includes Himalayan salt at 20-35%, aloe at 0.2-2%, carboxymethylcellulose 0.2-5%, soy at 0.5-3% and distilled water at 50-90%. Alginate, gelatin, starch or a combination thereof are added at 0.3-10%.

EXAMPLE 29

Another inventive formula includes Himalayan salt at 18-29%, aloe at 0.2-2%, soy at 0.5-3%, bentonite at 0.1-5% and distilled water at 50-90%.

EXAMPLE 30

Another inventive formula includes Himalayan salt at 20-30%, aloe at 0.2-2%, soy at 0.5-3%, carboxymethylcellulose 0.2-5%, bentonite at 0.1-5%, a few drops of frankincense oil and distilled water at 50-90%.

EXAMPLE 31

Another inventive formula includes Himalayan salt at 17-27%, aloe at 0.2-2%, soy at 0.5-3%, bentonite at 0.1-5%, carboxymethylcellulose 0.2-5%, a few drops of sandalwood oil and distilled water at 50-90%.

EXAMPLE 32

Another inventive formula includes Himalayan salt at 18-32%, aloe at 0.2-2%, soy at 0.5-3%, carboxymethylcellulose 0.2-5%, a few drops of both frankincense and sandalwood oils and distilled water at 50-90%.

EXAMPLE 33

Another inventive formula includes Himalayan salt at 19-29%, aloe at 0.2-2%, soy at 0.5-3%, carboxymethylcellulose 0.2-5%, turmeric and distilled water at 50-90%.

EXAMPLE 34

Another inventive formula includes Himalayan salt at 20-30%, aloe at 0.2-2%, soy at 0.5-3%, bentonite at 0.1-5%, carboxymethylcellulose 0.2-5%, and 0.5-2% moisturizing agents and distilled water at 50-90%.

The foregoing description is considered as illustrative only of the principles of the invention. Further, since numerous modifications and changes will readily occur to those skilled in the art, it is not desired to limit the invention to the exact construction and process shown and described above. Accordingly, all suitable modifications and equivalents may be resorted to falling within the scope of the invention.

For the purposes of promoting an understanding of the principles of the invention, reference will now be made to the exemplary embodiments illustrated in the drawings, and specific language will be used to describe the same. It will nevertheless be understood that no limitation of the scope of the invention is hereby intended. Any alterations and further modifications of the inventive features illustrated herein, and any additional application of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus appearances of the phrases an "embodiment," and "example," and similar language throughout this specification may, but do not necessarily, all refer to the same embodiment, to different embodiments, or to one or more of the figures. Additionally, reference to the words "embodiment," "example" or the like for two or more features, elements, etc., does not mean that the features are necessarily related, dissimilar, the same, etc.

Each statement of an embodiment or example is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment."

The features, functions and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional un-recited elements or method steps. "Comprising" is to be interpreted broadly and including the more restrictive terms "consisting of" and "consisting essentially of."

Reference throughout this specification to features, advantages, or similar language does not imply that all of features and advantages that may be realized with the present invention should be or are in any single embodiment of the invention. Rather, language referring to the features and advantages is understood to mean that a specific feature, advantage or characteristic described in connection with an embodiment is included in at least one embodiment of the present invention. Thus, discussion of the features and advantages, and similar language, throughout this specification may, but does not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized as certain embodiments that may not be present in all embodiments of the invention.

The invention claimed is:

1. A method for treating a medical condition chosen from poisoning or infection from a tattoo, the method comprising
    a) cleaning at least one surface of the tattoo;
    b) preparing a plurality of needles to administer a formulation comprising a solution comprising distilled water, aloe, carboxymethylcellulose, and about 15%-30% by weight salt;
    c) covering the surface of the tattoo and surrounding area with injections of the solution until the selected area has a different appearance of the tattoo;
    d) spreading the solution on the surface of the tattoo to provide a coating; and
    e) permitting the solution to dry.

2. The method of claim 1 in which the solution comprises distilled water, carboxymethylcellulose, aloe vera and less than about 30% by weight Himalayan salt.

3. The method of claim 1 further comprising the step of treating the tattooed area with an anesthetic introduced via cream before the skin is broken.

4. The method of claim 1 further comprising the step of injecting into the tattoo area an anesthetic liquid.

5. The method of claim 1 further comprising the step of allowing the solution to dry on the tattooed skin area for at least 15 minutes.

6. The method of claim 1 further comprising the step of allowing the solution to dry on the tattooed skin area for about 8-30 minutes.

* * * * *